(12) United States Patent
Wei et al.

(10) Patent No.: US 8,783,090 B2
(45) Date of Patent: Jul. 22, 2014

(54) APPARATUS AND METHODS FOR DETERMINATION OF TOTAL AND SOLID CARBON CONTENT OF ENGINE EXHAUST

(75) Inventors: Qiang Wei, San Antonio, TX (US); Imad Said Abdul-Khalek, San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 487 days.

(21) Appl. No.: 13/305,540

(22) Filed: Nov. 28, 2011

(65) Prior Publication Data

US 2013/0133308 A1    May 30, 2013

(51) Int. Cl.
| | |
|---|---|
| *G01N 1/38* | (2006.01) |
| *G01N 37/00* | (2006.01) |
| *G01N 31/12* | (2006.01) |
| *G01N 1/22* | (2006.01) |
| *G01M 15/10* | (2006.01) |

(52) U.S. Cl.
USPC ........................... 73/23.33; 436/133; 73/28.01

(58) Field of Classification Search
CPC ............ F02D 41/1452; F02D 41/1453; F02D 41/1466; G01N 1/2252; G01N 15/0618
USPC ..................... 73/23.31, 23.33, 28.01; 436/133
See application file for complete search history.

(56) References Cited

U.S. PATENT DOCUMENTS

| | | | | |
|---|---|---|---|---|
| 2,890,930 | A * | 6/1959 | Steele et al. ................... | 423/246 |
| 3,955,924 | A * | 5/1976 | Northmore et al. ............ | 436/146 |
| 5,279,970 | A * | 1/1994 | Patashnick et al. ........... | 436/133 |
| 5,546,788 | A * | 8/1996 | Dickow ....................... | 73/28.01 |
| 5,756,360 | A * | 5/1998 | Harvey et al. ................. | 436/179 |
| 6,151,952 | A * | 11/2000 | Mathews et al. ............. | 73/23.31 |
| 6,205,842 | B1 * | 3/2001 | Patashnick et al. .......... | 73/28.01 |
| 6,516,654 | B2 * | 2/2003 | Uchihara et al. ............. | 73/28.04 |
| 6,796,165 | B2 | 9/2004 | Abdul-Khalek | |
| 6,865,472 | B2 * | 3/2005 | Nakamura .................... | 701/108 |
| 7,647,810 | B2 * | 1/2010 | Wei et al. ..................... | 73/23.31 |
| 7,741,127 | B2 * | 6/2010 | Johnston Bartley et al. . | 436/181 |
| 8,079,838 | B2 * | 12/2011 | Wei ................................. | 425/6 |
| 8,474,304 | B2 * | 7/2013 | Knopf et al. ................. | 73/28.04 |

(Continued)

OTHER PUBLICATIONS

California Air Resources Board, El Monte, California—May 18, 2010; Public Workshop on Proposed Revisions to the Low-Emission Vehicle Program: Emission Limits for Particle Mass, Solid Particle Number, and Black Carbon; downloaded Feb. 17, 2012 from http://www.arb.ca.gov/msprog/levprog/leviii/meetings/051810/lev_iii_pm_and_bc_v2.pdf.

(Continued)

*Primary Examiner* — Lisa Caputo
*Assistant Examiner* — Punam Roy
(74) *Attorney, Agent, or Firm* — Grossman Tucker et al (57) ABSTRACT

The present disclosure provides apparatus and methods to determine real-time total carbon content, non-inclusive of carbon dioxide, and/or solid carbon content of engine exhaust. For a total carbon content determination, substantially all carbon dioxide is removed from the exhaust, and thereafter substantially all the remaining carbon of the exhaust is oxidized to provide a quantity of carbon dioxide which then may be used to determine total carbon content of the exhaust. For solid carbon content determination, in addition to substantially all carbon dioxide being removed from the exhaust, substantially all carbon-containing non-solid substances are also removed from the exhaust, and thereafter substantially all the remaining carbon of the exhaust is oxidized to provide a quantity of carbon dioxide which then may be used to determine solid carbon content of the exhaust.

29 Claims, 2 Drawing Sheets

(56) References Cited

U.S. PATENT DOCUMENTS

| | | | |
|---|---|---|---|
| 8,505,276 B2* | 8/2013 | Nakamura | 60/276 |
| 2003/0012700 A1* | 1/2003 | Carnahan | 422/102 |
| 2007/0131038 A1* | 6/2007 | Wei et al. | 73/865.5 |
| 2008/0148870 A1* | 6/2008 | Wei et al. | 73/863.61 |
| 2009/0003125 A1* | 1/2009 | Kusaka et al. | 366/160.1 |
| 2014/0093435 A1* | 4/2014 | Giechaskiel et al. | 422/170 |

OTHER PUBLICATIONS

California Air Resources Board, El Monte, California—May 18, 2010; Public Workshop—Preliminary Discussion Paper on Proposed Amendments to California's Low-Emission Vehicle Regulations—Particulate Matter Mass, Ultrafine Solid Particle Number, and Black Carbon Emissions; downloaded Feb. 17, 2012 from http://www.arb.ca.gov/msprog/levprog/leviii/meetings/051810/pm_disc_paper-v6.pdf.

* cited by examiner

APPARATUS AND METHODS FOR DETERMINATION OF TOTAL AND SOLID CARBON CONTENT OF ENGINE EXHAUST

FIELD OF THE INVENTION

The present disclosure relates generally to apparatus and methods to determine real-time total carbon content, non-inclusive of carbon dioxide, and/or solid carbon content of engine exhaust gas discharged from an internal combustion engine.

BACKGROUND

In the context of an internal combustion engine, internal combustion may be understood to particularly involve exothermic chemical reactions between a fuel and an oxidant accompanied by the production of heat and conversation of chemical species. The fuel may generally comprise organic compounds, especially hydrocarbons (HC), while the oxidant may generally comprise oxygen ($O_2$). With a proper stoichiometric ratio, complete combustion may be understood to result in the production of carbon dioxide ($CO_2$) and water ($H_2O$), as may be shown by the following reaction:

$$C_aH_b + (a+b/4)(O_2 + 3.773N_2) = aCO_2 + (b/2)H_2O + 3.773(a+b/4)N_2$$

However, complete combustion is often difficult to achieve. Consequently, from incomplete or partial oxidation/combustion, as well as contaminates entering an engine cylinder (e.g. engine lubricating oil), exhaust emissions may include carbon-containing substances in non-solid form, such as liquid/vapor or gas form (e.g. hydrocarbon compounds from fuel and/or oil, and carbon monoxide), as well as carbon-containing substances in solid form (e.g. soot).

Particulate matter (PM) emitted from an internal combustion engine, such as a diesel engine, may be generally composed of volatile and solid fractions. The solid fraction may mainly comprise carbon and a small amount of inorganic ash. The carbon of soot has historically been referred to as being amorphous, but may better be considered polycrystalline or nanocrystalline materials of graphite or diamond within an amorphous carbon matrix.

The volatile fraction of particulate matter may consist of unburned and partially burned hydrocarbons (e.g. from fuel and lubricating oil), and sulfur compounds. Dry soot particles (i.e. solid) may be formed in the combustion chamber of an engine while most of the volatile fraction of the particulate matter enters the particle phase from the gas phase as the exhaust cools. The particle phase of the volatile fraction consists of precipitated liquid particles and precipitated liquid that attach to preexisting solid particles, which may be referred to as "wet" soot. Hence, particulate matter is a combined measure of solid and volatile fractions.

Depending upon operating conditions, an internal combustion engine may emit exhaust emissions containing a large amount of soot. The soot may cause adverse environmental and human health concerns. For example, with regards to environmental concerns, soot may contribute to global warming. As for human health concerns, soot may include carcinogenic substances and cause diseases affecting the human respiratory system. Furthermore, the U.S. Environmental Protection Agency (EPA) has set forth that engine exhaust may increase morbidity. As a result, the California Air Resource Board (CARB) has proposed a Low Emission Vehicle (LEV) III standard to further reduce gaseous and particulate matter emissions from light-duty and medium-duty vehicles. Black Carbon (BC), which may be a primary component of the soot, may be added for the carbon dioxide equivalency calculation.

To better study environmental and health concerns related to exhaust generated by internal combustion engines, there has been a need to be better characterize exhaust emissions, and more particularly soot emissions. Instruments have been developed to measure soot particle size distributions, soot particle surface areas, and soot particle mass emissions concentration. Furthermore, since mass-based particulate matter emissions remain an important criteria regulated by regulatory agencies, instruments which are able to measure soot mass emission in real-time are in demand by industry, regulatory agencies, and academic institutes.

Several instruments are commercially available for real-time soot particle mass emissions concentration determination. A photo-acoustic sensor is one technology which may be used for soot mass concentration determination. The photo-acoustic sensor may be understood to measure real-time soot particle mass emissions concentration with a photo-acoustic principle. A modulated laser beam heats soot particles, and then the soot particles are allowed to cool by turning off the laser beam. A sensitive microphone measures sound signals generated by the process of heating and cooling of the soot particles. Then, the sound signals measured by the microphone may be converted to a soot volume concentration. To ensure the accuracy of the measurement, it may be necessary to calibrate the instrument with soot particles by using a gravimetric filter method.

Laser Induced Incandescence (LII) is another major technology which may be used for real-time soot mass measurement from flames and internal combustion engines. A high intensity laser may be applied to heat soot particles to a temperature close to the soot particle sublimation temperature. Radiation of the soot particles during the cooling process is recorded. Then it is compared to a well defined cooling process which is obtained from a mathematic model. From there, the average diameter of the primary soot particle in soot clusters is obtained. Finally, soot volume may be calculated from the diameter of the primary particle and other parameters. To make this instrument work correctly, it may have to be calibrated against other soot measurement instruments or gravimetric filter measurement.

However, the foregoing technologies used for real-time soot mass measurement are not understood to provide a direct correlation to soot volume or mass. The conversion of a measured signal to the soot mass for those instruments is normally based on limited empirical data and many assumptions. Those empirical data and assumptions may be satisfactory under some conditions, but not all conditions. The foregoing technologies may be sensitive to engine technology, gas compositions, particle size distributions, etc. Moreover, since there are no particulate matter reference standards available, calibration procedures for these technologies may be complicated, time-consuming, and may produce different results among laboratories. Furthermore, calibration may require that the operator have a good technical background for the instrument and aerosol science. Additionally, soot mass results determined with these technologies may be questioned in that the instruments may not be calibrated as frequently as may be required, particularly in light of difficult calibration procedures.

In light of the above, an apparatus to determine total and solid carbon content, that may be easy to calibrate using traceable devices and commonly used standard operating procedures, is needed to overcome the aforementioned difficulties in the art.

SUMMARY

The present disclosure provides apparatus and methods to determine real-time total carbon content (mass concentration), non-inclusive of carbon dioxide, or solid carbon content (mass concentration) of engine exhaust. By operating the apparatus in different modes, the apparatus can either determine real-time total carbon content, or real-time solid carbon content. Since the apparatus herein may determine real-time total carbon content or real-time solid carbon content with a good accuracy, such may be used as a reference to calibrate other apparatus and sensors.

In an embodiment of the disclosure, to determine real-time total carbon content (mass concentration), non-inclusive of carbon dioxide, the exhaust may first have at least a substantial portion of the initial carbon dioxide of the exhaust removed from the exhaust, such as by a carbon dioxide adsorber. The exhaust may then be heated to a temperature and in a presence of oxygen to oxidize substantially all the carbon remaining of the exhaust and generate a quantity of carbon dioxide thereby. Then, real-time total carbon content (mass concentration) of the exhaust, non-inclusive of carbon dioxide, may be determined (calculated) from the quantity of generated carbon dioxide and the chemical balance of the carbon oxidation in oxygen, which may include adjustment for dilution during the process and residual initial carbon dioxide content of the exhaust.

In an embodiment of the disclosure, to determine real-time solid carbon content (mass concentration), the exhaust may first be heated to a temperature and in a presence of oxygen to oxidize substantially all the carbon of carbon-containing non-solid substances of the exhaust, without oxidizing carbon of carbon-containing solid particles of the exhaust. The exhaust may then have at least a substantial portion of the initial carbon dioxide of the exhaust removed from the exhaust, such as by a carbon dioxide adsorber. The exhaust may then be heated to a temperature and in a presence of oxygen to oxidize substantially all the carbon of the carbon-containing solid particles of the exhaust and generate a quantity of carbon dioxide thereby. Then, real-time solid carbon content (mass concentration) of the exhaust may be determined (calculated) from the generated carbon dioxide and the chemical balance of the carbon oxidation in oxygen, which may include adjustment for dilution during the process and residual initial carbon dioxide content of the exhaust.

In an embodiment of the disclosure, a method to determine total carbon content, non-inclusive of carbon dioxide, of internal combustion engine exhaust is provided, with the method comprising: obtaining an engine exhaust sample from an internal combustion engine of a motor vehicle, the engine exhaust sample including carbon dioxide and one or more additional carbon-containing substances; diluting the exhaust sample with a diluent, wherein the diluent cools the exhaust sample and reduces a concentration of the carbon dioxide of the exhaust sample; removing at least a substantial portion of the carbon dioxide from at least a portion of the exhaust sample to provide an exhaust test specimen; heating the exhaust test specimen in a heating device to a temperature and in a presence of oxygen to oxidize substantially all the carbon of the one or more additional carbon-containing substances of the exhaust test specimen and generating carbon dioxide thereby; cooling the exhaust test specimen in a cooling device, determining an overall quantity of carbon dioxide of the exhaust test specimen; and determining an overall quantity of carbon of the exhaust test specimen using the overall quantity of carbon dioxide of the exhaust test specimen. And thereafter, determining an overall concentration of carbon of the exhaust sample using the overall quantity of carbon of the exhaust test specimen.

In various embodiments of the disclosure, the method may further comprise determining an overall concentration of carbon of the exhaust sample using the overall quantity of carbon of the exhaust test specimen.

In various embodiments of the disclosure, the method may further comprise, after removing at least a substantial portion of the carbon dioxide from at least a portion of the exhaust sample to provide an exhaust test specimen, determining whether the exhaust test specimen includes a residual quantity of carbon dioxide. Furthermore, the method may further comprise, after determining whether the exhaust test specimen includes a residual quantity of carbon dioxide, if the test specimen includes a residual quantity of carbon dioxide, then subtracting the residual quantity of carbon dioxide of the exhaust test specimen from the overall quantity of carbon dioxide of the exhaust test specimen to determine an adjusted quantity of carbon dioxide of the exhaust test specimen, and determining an adjusted quantity of carbon of the exhaust test specimen using the adjusted quantity of carbon dioxide of the exhaust test specimen. Furthermore, the method may further comprise determining an adjusted concentration of carbon of the exhaust sample using the adjusted quantity of carbon of the exhaust test specimen.

In various embodiments of the disclosure, the method may further comprise determining whether the exhaust test specimen includes a residual quantity of carbon dioxide is performed with a carbon dioxide analyzer.

In various embodiments of the disclosure, the method may further comprise filtering the exhaust test specimen before determining whether the exhaust test specimen includes a residual quantity of carbon dioxide.

In various embodiments of the disclosure, the method may further comprise removing water from the exhaust test specimen before determining whether the exhaust test specimen includes a residual quantity of carbon dioxide.

In various embodiments of the disclosure, the one or more additional carbon-containing substances may comprise at least one of carbon monoxide, one or more hydrocarbon compounds, and carbon-containing solid particles comprising one or more solid carbonaceous substances.

In various embodiments of the disclosure, the diluent cools the exhaust sample to a temperature in a range between 20° C. to 55° C.

In various embodiments of the disclosure, the diluent comprises at least one of pure oxygen and purified air.

In various embodiments of the disclosure, the method further comprises removing at least a substantial portion of the carbon dioxide from at least a portion of the exhaust sample to provide an exhaust test specimen is performed with at least one carbon dioxide adsorber.

In various embodiments of the disclosure, the at least one carbon dioxide adsorber comprises a plurality of carbon dioxide adsorbers arranged to be operated in series.

In various embodiments of the disclosure, the method may further comprise removing at least a substantial portion of the carbon dioxide from at least a portion of the exhaust sample to provide an exhaust test specimen further comprises removing at least 95% by weight of the carbon dioxide.

In various embodiments of the disclosure, the method may further comprise heating the exhaust test specimen in a heating device in a presence of oxygen is performed with oxygen initially of the exhaust sample, oxygen added to the exhaust sample and/or oxygen added to exhaust test specimen.

In various embodiments of the disclosure, the oxygen added to the exhaust sample and/or the exhaust test specimen is provided from at least one of pure oxygen and purified air.

In various embodiments of the disclosure, the method may further comprise heating the exhaust test specimen in a heating device to a temperature and in a presence of oxygen to oxidize at least 95% by weight of the carbon of the one or more additional carbon-containing substances of the exhaust test specimen and generating carbon dioxide thereby.

In various embodiments of the disclosure, the cooling device cools the exhaust test specimen to a temperature in a range between 20° C. to 55° C.

In various embodiments of the disclosure, the method may further comprise determining an overall quantity of carbon dioxide of the exhaust test specimen is performed with a carbon dioxide analyzer.

In various embodiments of the disclosure, the method further comprises filtering the exhaust test specimen after cooling the exhaust test specimen in a cooling device, and before determining an overall quantity of carbon dioxide of the exhaust test specimen.

In another embodiment of the disclosure, a method to determine solid carbon content of internal combustion engine exhaust is provided, with the method comprising: obtaining an engine exhaust sample from an internal combustion engine of a motor vehicle, the engine exhaust sample including carbon dioxide, carbon-containing solid particles comprising one or more solid carbonaceous substances and one or more additional carbon-containing non-solid substances; heating the exhaust sample in a first heating device to a temperature and in a presence of oxygen to oxidize substantially all the carbon of the one or more additional carbon-containing non-solid substances of the exhaust sample and generating carbon dioxide thereby; diluting the exhaust sample with a diluent, wherein the diluent cools the exhaust sample and reduces a concentration of the carbon dioxide of the exhaust sample; removing at least a substantial portion of the carbon dioxide from at least a portion of the exhaust sample to provide an exhaust test specimen; heating the exhaust test specimen in a second heating device to a temperature and in a presence of oxygen to oxidize substantially all the carbon of the carbon-containing solid particles of the exhaust test specimen and generating carbon dioxide thereby; cooling the exhaust test specimen in a cooling device, determining an overall quantity of carbon dioxide of the exhaust test specimen; and determining an overall quantity of carbon of the exhaust test specimen using the overall quantity of carbon dioxide of the exhaust test specimen. And thereafter, determining an overall concentration of carbon of the carbon-containing solid particles of the exhaust sample using the overall quantity of carbon of the exhaust test specimen.

In various embodiments of the disclosure, the method may further comprise determining an overall concentration of carbon of the carbon-containing solid particles of the exhaust sample using the overall quantity of carbon of the exhaust test specimen.

In various embodiments of the disclosure, the method may further comprise, after removing at least a substantial portion of the carbon dioxide from at least a portion of the exhaust sample to provide an exhaust test specimen, determining whether the exhaust test specimen includes a residual quantity of carbon dioxide. Furthermore, the method may further comprise, after determining whether the exhaust test specimen includes a residual quantity of carbon dioxide, if the test specimen includes a residual quantity of carbon dioxide, then subtracting the residual quantity of carbon dioxide of the exhaust test specimen from the overall quantity of carbon dioxide of the exhaust test specimen to determine an adjusted quantity of carbon dioxide of the exhaust test specimen, and determining an adjusted quantity of carbon of the exhaust test specimen using the adjusted quantity of carbon dioxide of the exhaust test specimen. Furthermore, the method may further comprise determining an adjusted concentration of carbon of the carbon-containing solid particles of the exhaust sample using the adjusted quantity of carbon of the exhaust test specimen.

In various embodiments of the disclosure, one or more additional carbon-containing non-solid substances comprise at least one of carbon monoxide in gas form and one or more hydrocarbon compounds in gaseous or liquid form.

In various embodiments of the disclosure, the carbon-containing solid particles may comprise solid soot particles and/or elemental carbon.

In another embodiment of the disclosure, an apparatus to determine carbon content in internal combustion engine exhaust is provided, with the apparatus comprising: an inlet configured to obtain an engine exhaust sample from an internal combustion engine of a motor vehicle; a first heating device configured to receive the exhaust sample from the inlet, and heat the exhaust sample to a temperature and in a presence of oxygen to oxidize carbon of one or more carbon-containing non-solid substances of the exhaust sample without oxidizing carbon-containing solid particles of the exhaust sample; a diluter configured to receive the exhaust sample from the first heating device, and to dilute the exhaust sample with a diluent which cools the exhaust sample and reduces a concentration of carbon dioxide of the exhaust sample; at least one carbon dioxide adsorber configured to receive the exhaust sample from the diluter, and to remove carbon dioxide from at least a portion of the exhaust sample to provide an exhaust test specimen; a second heating device configured to receive the exhaust test specimen, and heat the exhaust test specimen to a temperature and in a presence of oxygen to oxidize carbon of carbon-containing solid particles of the exhaust test specimen; a cooling device configured to receive the exhaust test specimen from the second heating device, and cool the exhaust test specimen, a carbon dioxide analyzer configured to receive the exhaust test specimen from the cooling device, and to determine an overall quantity of carbon dioxide of the exhaust test specimen; and a computer device configured to determine an overall quantity of carbon of the exhaust test specimen using the overall quantity of carbon dioxide of the exhaust test specimen. The computer device may be further configured to determine an overall concentration of carbon of the carbon-containing solid particles of the exhaust sample using the overall quantity of carbon of the exhaust test specimen.

FIGURES

The above-mentioned and other features of this disclosure, and the manner of attaining them, will become more apparent and better understood by reference to the following description of embodiments described herein taken in conjunction with the accompanying drawings, wherein.

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

While a preferred embodiment(s) of the present invention(s) have been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

Figure 1:
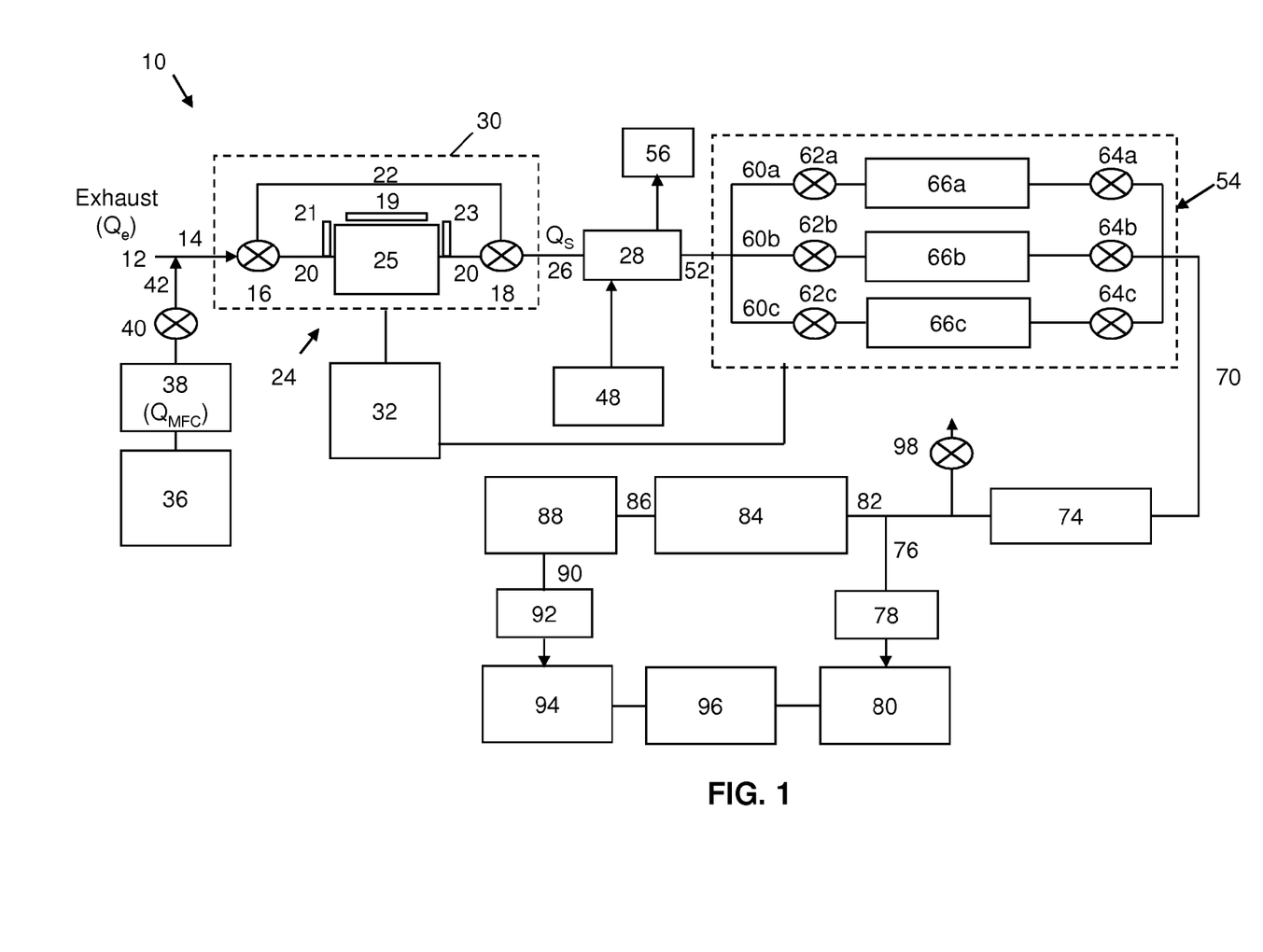
FIG. 1 illustrates a flow schematic for an apparatus to determine total carbon or solid carbon content with the apparatus and methods according to one embodiment of the present disclosure.

Referring now to FIG. 1, there is show a flow schematic for a an apparatus 10 to determine carbon content of engine exhaust according to the present disclosure, which may particularly determine carbon content of internal combustion engine exhaust, such as of a diesel engine, of a motor vehicle. Apparatus 10 may determine real-time total carbon content, non-inclusive of carbon dioxide, or solid carbon content of internal combustion engine exhaust.

During operation of apparatus 10, a flow of engine exhaust Qe may enter the apparatus 10 at apparatus inlet opening 12. Inlet opening 12 may be particularly configured to be in fluid communication with and obtain an engine exhaust sample from an exhaust system of an internal combustion engine of a motor vehicle. The engine exhaust sample may include carbon dioxide gas, carbon-containing solid particles, particularly comprising one or more solid carbonaceous substances, and one or more additional carbon-containing non-solid substances (i.e. in addition to carbon dioxide gas).

For example, carbon-containing solid particles may include solid dry soot particles (e.g. the carbon solid fraction of soot), and one or more solid carbonaceous substances may include elemental carbon. Other than carbon dioxide, carbon-containing non-solid substances may include liquid/vapor or gas forms of hydrocarbon compounds and carbon monoxide. Hydrocarbon compounds may be unburned or partially burned, and may originate from fuel and lubricating oil. Liquid hydrocarbon compounds may be in the form of precipitated liquid particles, and precipitated liquid that is attached to solid, dry soot particles, so as to form carbonaceous primary (nuclei) particles having a core of soot with an outer member of hydrocarbons, which may be referred to as wet soot. Hydrocarbons in the gas phase and particle phase may include polynuclear aromatic hydrocarbons (PAH), which may contain two or more benzene rings.

After entering inlet opening 12, the engine exhaust may flow through flow passage 14. In order to inhibit significant solid particle losses, such as soot, from the engine exhaust within flow passage 14, which may be particularly due to solid particles adhering to the inner surfaces of apparatus 10, the inner surfaces of flow passage 14, as well as the surfaces of the remainder of the components of apparatus 10 exposed to the engine exhaust, may be made of an electrically conductive material, such as stainless steel. Apparatus 10 may particularly have a total solid particle loss from the time the particles enter the apparatus to the time the solid particles are oxidized in second heating device 84, as explained in greater detail below, of less than 10% by weight, and more particularly less than 5% by weight, and even more particularly less than 2% by weight.

The solid particles of the engine exhaust which enter apparatus 10 may be understood to carry an electrical charge, either positive (+) or negative (−). Upon contact with an electrically conductive surface of apparatus 10, the electrically conductive nature of the surface of apparatus 10 may be understood to neutralize the charge, thus reducing the likelihood of the solid particle sticking to a surface of apparatus 10, such as due to the attraction of opposite charges.

After flowing through flow passage 14, the engine exhaust may thereafter enter valve 16. Valve 16, as well as valve 18, may particularly be high temperature valves that allow the engine exhaust to pass through while inhibiting carbon-containing solid particle losses, particularly of soot, therein. Opening and closing of valves 16 and 18 may be controlled manually or automatically by a controller 32. Valves 16 and 18 may particularly comprise three-way ball valves.

As shown, two flow passages 20 and 22 exist between valves 16 and 18, with flow passage 20 in fluid communication with a first heating device 24 and flow passage 22 bypassing heating device 24. During a determination of total carbon content of the engine exhaust, as explained in greater detail below, valves 16 and 18 may be closed to flow passage 20 and opened to flow passage/bypass 22 for the flow of engine exhaust to subsequently flow through flow passages 22 and 26 to a diluter 28.

During a determination of solid carbon content of the engine exhaust, the engine exhaust may be directed through heating device 24 by controlling valves 16 and 18, manually or automatically, so as to open flow passage 20 and close flow passage 22. More particularly, to determine solid carbon content of the engine exhaust, heating device 24 may be particularly configured to receive the exhaust from the inlet 12 via passages 14 and 20, and heat the exhaust to a temperature and in a presence of oxygen to oxidize substantially all (e.g. at least 95% by weight) the carbon of one or more carbon-containing non-solid substances of the exhaust, without oxidizing the carbon of carbon-containing solid particles of the exhaust sample.

More particularly, heating device 24 may particularly be a catalytic stripper device which contains one or more oxidation catalysts 25 to oxidize hydrocarbons and carbon monoxide in the engine exhaust into carbon dioxide under high temperature conditions. Again, the temperature/heating conditions may be understood to be high enough to result in oxidation of hydrocarbons and carbon monoxide in the engine exhaust, but low enough such that carbon of the carbon-containing solid particles therein may not be oxidized.

Heating device 24 may have an oxidation catalyst 25 such as a Diesel Oxidation Catalyst (DOC) having a platinum-loaded honeycomb structure. A flow-thru catalyst substrate may be designed to provide enough residence time for unburned and partially burned fuel and lube oil hydrocarbon and carbon monoxide molecules to diffuse to the internal surface of the substrate channels and become oxidized. Again, the oxidation catalyst 25 strips hydrocarbon molecules from the exhaust through conversion of hydrocarbon to carbon dioxide and water, and strips carbon monoxide molecules from the exhaust through conversion of carbon monoxide to carbon dioxide, Other components of the heating device 24 include a first temperature sensor 21 disposed in the flow passage 20 at a position adjacent an inlet end of the catalyst 25, and a second temperature sensor 23 disposed in the flow passage 20 at an outlet end of the catalyst 25. The heating device 24 also includes a heater 19, such as a resistance cartridge heater, disposed in intimate contact with the catalyst 25 to heat the catalyst to a selected temperature. A controller 32, which may include a temperature controller, is in electrical communication with at least one of the temperature sensors 21, 23 and with the heater 19. The heater 19 and the controller 32 controllably heats and maintains the catalyst 25 at a temperature within a range of from about 250° C. to about 500° C., and more particularly about 350° C. to oxidize the hydrocarbons and carbon monoxide.

Since volatile particulate matter precursors, such as gas phase hydrocarbons, may be removed by the heating device 24, the heating device 24 inhibits volatile particulate matter from forming during subsequent dilution and cooling of the engine exhaust. Thereafter, the engine exhaust with the remaining carbon-containing solid particles may exit the heating device 24 and flow through flow passage 26 into the diluter 28 downstream of valve 18. In the foregoing manner, it may be understood that substantially all carbon of containing non-solid substances may be removed from the engine exhaust, non-inclusive of carbon dioxide and carbon of carbon-containing solid particles.

To further inhibit significant carbon-containing solid particle losses, particularly of soot, from the engine exhaust within carbon measurement apparatus 10, such as by thermophoretic mechanism, all components in dashed square 30, which may include the heating device 24 and flow passage/bypass 22 may be particularly heated and insulated. Temperatures for the individual components in the dashed square 30 may be individually controlled by a controller 32 to each be at a same or different temperatures.

Under some circumstances, such as when engine exhaust is emitted by an engine operating at rich or stoichiometric air-fuel conditions, oxygen content initially in the engine exhaust may be understood to be close to zero. Thus, hydrocarbons and carbon monoxide may not be removed by the heating device 24 by oxidation since there is substantially no oxygen available for oxidizing hydrocarbon and carbon monoxide into carbon dioxide. In addition, to oxidize the carbon of carbon-containing solid particles downstream in a second heating device 84, discussed in greater detail below, the presence of oxygen is necessary as well.

In order for apparatus 10 to better work properly under very low or no oxygen conditions, a gas oxidizer source 36 comprising oxygen, a mass flow controller 38, valve 40 and inlet flow passage 42, which is in fluid communication with flow passage 14, may be installed upstream of valve 16. Gas oxidizer source 36 may be provided by compressed pure oxygen or carbon-free purified air, or a mixture thereof.

Carbon-free purified air may be understood to be purified ambient (natural) or synthetic air (i.e. the components are mixed together by man as opposed to being mixed in nature), with negligible concentration of contaminants, such as gaseous carbon dioxide, carbon monoxide, hydrocarbons, and nitrogen oxides, as well as solid particles such as soot. More particularly, carbon-free purified air may be understood to contain less than 0.1 parts per million carbon, and have a composition made up of at least about 99 percent nitrogen and oxygen by weight, with the composition comprising about 78 percent nitrogen by weight, and about 21 percent oxygen by weight. Other components of carbon-free purified air may include inert or rare gases such as argon, which may be generally present at less than about 1 percent by weight. Purified air may also include carbon zero air which essentially consists of, or consists of, nitrogen and oxygen.

Introduction of a flow of gas oxidizer $Q_{MFC}$ from gas oxidizer source 36 may be controlled by the mass flow controller 38. The flow of gas oxidizer $Q_{MFC}$ may be added to the engine exhaust sufficiently such that all the hydrocarbons and carbon monoxide in the engine exhaust may be oxidized by the oxygen provided by gas oxidizer source 36. With the addition of a gas oxidizer, the apparatus 10 is capable of measuring total carbon or solid carbon content of engine exhaust when the oxygen concentration thereof is close to zero.

A primary function of valve 40 is to shut off the flow of gas oxidizer $Q_{MFC}$ from gas oxidizer source 36 into the apparatus 10, particularly in the event the mass flow controller 38 may not completely shut off the flow of gas oxidizer $Q_{MFC}$. When there is no need to add oxygen into the apparatus 10, valve 40 is closed and the flow of gas oxidizer $Q_{MFC}$ on the mass flow controller 38 may be understood to be zero.

Once the flow of engine exhaust Qe mixes and reacts with the flow of gas oxidizer $Q_{MFC}$ in heating device 24, the resulting flow of engine exhaust exiting from the heating device 24, which may be referred to as Qs, and flowing into the diluter 28 downstream of valve 18 may be measured by the diluter 28. Furthermore, since the flow of gas oxidizer $Q_{MFC}$ from gas oxidizer source 36 passing through mass flow controller 38 may also be measured, a first dilution ratio $DR_1$ due to adding the flow of gas oxidizer $Q_{MFC}$ from gas oxidizer source 36 to the flow of engine exhaust Qe may be determined.

Diluter 28 is configured to receive either the exhaust via flow passage 20 which is in fluid communication with heating device 24, or flow passage 22 which bypasses heating device 24. In either case, the exhaust gas may be raw (undiluted) or diluted by gas oxidizer source 36.

In addition to diluter 28 being configured to receive exhaust from heating device 24, diluter 28 is configured to dilute the exhaust with a diluent which cools the exhaust and reduces a concentration of carbon dioxide of the exhaust sample. More particularly, diluter 28 is used to dilute the engine exhaust which flows from valve 18 and into diluter 28 from flow passage 26. A gas diluent may be introduced into diluter 28 from a gas diluent source 48. Similar to the gas oxidizer, the gas diluent may be provided by compressed pure oxygen or carbon-free purified air, or a mixture thereof.

Diluter 28 adds the gas diluent, and quickly further dilutes the once diluted sample, or the raw exhaust, to bring the diluted sample to a temperature in a range between and including all increments between 20° C. to 55° C., and particularly less than 52° C. and more particularly about 25° C. Rapid cooling may also inhibit the formation of sulfuric acid particles, and reduces the thermophoretic deposition of particles on walls of the several components of apparatus 10.

The diluter 28 may control and measure the flow of gas diluent from gas diluent source 48 to mix therein with the engine exhaust exiting from the heating device 24. Similar to heating device 24, diluter 28 may dilute the engine exhaust exiting from the heating device 24 while inhibiting significant carbon-containing solid particle losses, particularly of soot, therefrom.

The inlet flow of the flow of engine exhaust exiting from heating device 24 into the diluter 28 from flow passage 26 may controlled and measured directly or indirectly by diluter 28. As a result of the foregoing dilution(s) of the flow of engine exhaust Qe, dilution ratios in the apparatus 10 may be defined in Equations 1 and 2 as follows:

$$DR_1 = \frac{Q_S}{Q_S - Q_{MFC}} \quad \text{(Equation 1)}$$

$$DR = DR_1 \times DR_2 \quad \text{(Equation 2)}$$

For equation (1), $DR_1$ may be understood as the dilution ratio associated with adding gas oxidizer from gas oxidizer source 36 of apparatus 10, while $DR_2$ may be understood as the dilution ratio associated with adding the gas diluent from gas diluent source 48 at diluter 28 of apparatus 10. It is observed from Equation 1 that the $DR_1$ is 1.0 if no gas oxidizer is added into the apparatus from gas oxidizer source 36.

At the outlet of the diluter 28, a small fraction of the of engine exhaust from the heating device 24 diluted by gas diluent from gas diluent source 48 may flow into flow passage 52 and carbon dioxide adsorber assembly 54. The remaining fraction of the diluted flow of engine exhaust from the stripper assembly Qs may be expelled through vent 56 of diluter 28. In alternative embodiments, the whole quantity of engine exhaust may be introduced to the carbon dioxide adsorber assembly 54.

Carbon dioxide adsorber assembly 54 is configured to receive at least a fraction of diluted exhaust from the diluter 28, and to remove a substantial portion (e.g. at least 95% by weight) of carbon dioxide from the fraction of the exhaust to provide an exhaust test specimen. The carbon dioxide adsorbing material within the carbon dioxide adsorber assembly may include, for example, solid sodium hydroxide. Carbon dioxide adsorbing material may also include calcium hydroxide and/or potassium hydroxide.

The carbon dioxide adsorber assembly 54 is used to reduce carbon dioxide in the flow of diluted engine exhaust to a lower level. In the carbon dioxide adsorber assembly 54, one or more carbon dioxide adsorber branches 60*a-c* may be employed. There are two valves, an inlet valve 62*a-c* and an outlet valve 64*a-c* for each carbon dioxide adsorber 66*a-c* in each branch 60*a-c*. By operating the valves 62*a-c* and 64*a-c* either manually or automatically, such as by controller 32, a branch 60*a-c* can be activated or disabled. For the case that one branch 60*a* only is in the carbon dioxide adsorber assembly 54, there is no need to install valve 62*a*, 64*a* upstream and downstream, respectively, of the carbon dioxide adsorber assembly 54.

The carbon dioxide adsorber assembly 54 may particularly be a device that adsorbs carbon dioxide from the diluted engine exhaust mixture of carbon dioxide and carbon-containing solid particles while inhibiting significant particle losses. The carbon dioxide adsorber assembly 54 may particularly have a high reduction efficiency for carbon dioxide. Thus, ideally, at the outlet of the carbon dioxide adsorber assembly 54 into flow passage 70, at least a substantial portion of the carbon dioxide should be removed from at least a portion of the exhaust sample to provide an exhaust test specimen.

To operate the adsorber assembly 54, one branch 60*a* only in the carbon dioxide adsorber assembly 54 may be activated at a particular time. Once the carbon dioxide adsorber 66*a* in the first activated branch 60*a* reaches the maximum capacity for carbon dioxide, carbon dioxide adsorber assembly 54 activates a second branch 60*b* by opening valves 62*b*, 64*b* and disables the used branch 60*a* by closing valves 62*a*, 64*a* on involved branches 60*a* and 60*b* manually or automatically. In the foregoing manner, the carbon dioxide adsorbers are arranged to be operated in series, but may also be operated in parallel. The disabled carbon dioxide adsorber 66*a* that reaches the carbon dioxide storage limit may thereafter be replaced or regenerated.

Once the carbon dioxide has been removed from the diluted exhaust by carbon dioxide adsorber assembly, an exhaust test specimen is now provided which may be used to ultimately determine either total carbon content or solid carbon content of the engine exhaust.

However, before the exhaust test specimen may be used, water vapor which may be present in engine exhaust prior to entering the apparatus 10, which may be generated in an catalytic converter of a motor vehicle's exhaust system, and/or which may be generated in heating device 24, and/or which may be generated in the carbon dioxide adsorber assembly 54, may interfere with carbon dioxide measurement in the carbon dioxide analyzer(s) 80, 94 downstream. Consequently, upon exiting the carbon dioxide adsorber assembly 54, it may be necessary to remove water vapor from the exhaust test specimen to better ensure accurate carbon dioxide measurement with carbon dioxide analyzer(s) 80, 94. To remove the water vapor, upon exiting the outlet of the carbon dioxide adsorber assembly 54, the exhaust test specimen may flow in flow passage 70 and into diffusion dryer 74. In the diffusion dryer 74, diffusion dryer 74 may remove water vapor while inhibiting significant particle losses.

At the outlet of the diffusion dryer 74, a very small portion of the exhaust test specimen may flow through flow passage 76 and into high-efficiency particulate air (HEPA) filter 78. Particles in the exhaust test specimen may be removed by high-efficiency particulate filter 78 before the flow of the exhaust test specimen enters carbon dioxide analyzer 80.

Carbon dioxide that passes through the carbon dioxide adsorber assembly 54 may be measured with carbon dioxide analyzer 80. In this manner, carbon dioxide analyzer 80 may be used to determine if the exhaust test specimen contains residual carbon dioxide which was not removed by carbon dioxide adsorber assembly 54.

Figure 2:
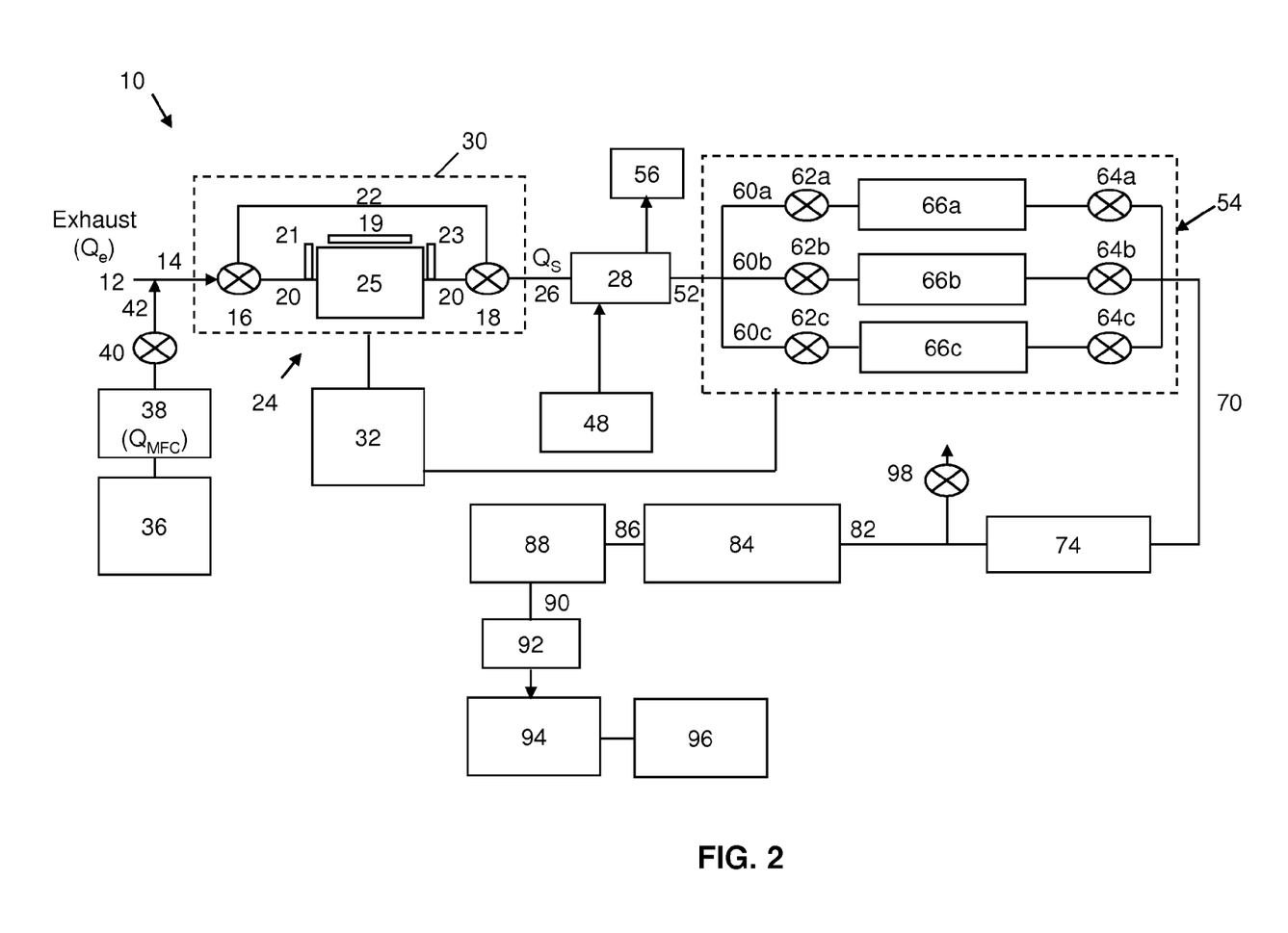
FIG. 2 illustrates a flow schematic for an apparatus to determine total carbon or solid carbon content with the apparatus and methods according to another embodiment of the present disclosure.

Carbon dioxide analyzer 80 may be a very sensitive analyzer that can measure very low carbon dioxide concentration such as at a part per billion (ppb) level. Under some circumstances, the carbon dioxide adsorber assembly 54 may completely remove carbon dioxide in the flow of engine exhaust, or remove such to a negligible level (e.g. less than 10 ppm (parts per million) by weight). In such an instance, it would be unnecessary to measure the carbon dioxide concentration at the outlet of the diffusion dryer 74. In other words, carbon dioxide analyzer 80 and high-efficiency particulate filter 78 could be removed from the apparatus 10. FIG. 2 presents the flow schematic without carbon dioxide analyzer 80 and high-efficiency particulate filter 78. Alternatively, the tasks of carbon dioxide analyzer 80 may also be performed by carbon dioxide analyzer 94.

The remaining fraction of the exhaust test specimen flows through flow passage 82 into a second heating device 84, which may be in the form of a high temperature oven. Second heating device 84 is configured to receive the exhaust test specimen, and heat the exhaust test specimen to a temperature and in a presence of oxygen to oxidize substantially all (e.g. at least 95% by weight) of the carbon of carbon-containing solid particles of the exhaust test specimen. The temperature of second heating device 84 may be controlled to be at a temperature where carbon-containing solid particles including soot particles may be oxidized into carbon dioxide gas completely. If additional gas oxidizer (oxygen is required) to be added to the exhaust test specimen, the gas oxidizer may be provided by compressed pure oxygen or carbon-free purified air, or a mixture thereof, particularly from gas oxidizer source 36.

For measurement of total carbon content, the carbon of carbon-containing non-solid substances has not been removed from the exhaust test specimen since the exhaust used to prepare the exhaust test specimen bypassed the first heating device 24. Total carbon content, non-inclusive of carbon dioxide, may include carbon of carbon-containing solid particles, which may include solid soot particles (e.g. the carbon solid fraction of soot), as well as carbon of the carbon-containing non-solid substances, which may include liquid/vapor or gas forms of hydrocarbon compounds and carbon monoxide. Thus, for in the case of total carbon measurement, a second heating device 84 may be understood to oxidize substantially all (e.g. at least 95% by weight) of the carbon of both carbon-containing non-solid substances as well as carbon-containing solid particles. Thus, in second heating device 84, all components containing carbon may be oxidized into carbon dioxide.

At the outlet of the second heating device 84, the exhaust test specimen may flow though flow passage 86 and into a cooling device 88, which may be a heat exchanger including a cooling coil with a circulating coolant (refrigerant) therein. Cooling device 88 may cool the engine exhaust from the second heating device 84 to a temperature in a range between 20° C. to 55° C. before the engine exhaust test specimen flows through flow passage 90 and into high-efficiency particulate filter 92 and subsequently carbon dioxide analyzer 94.

High-efficiency particulate filter 92 may remove non-carbon containing particles, which may include metal added to engine lube oil as a metal additive, some of which may be involved in combustion in engine cylinders and end up in the flow of exhaust gas. Generally, such residual particles have very high melting points, and may not be removed by the second heating device 84. Thus, it may be necessary to install a high-efficiency particulate filter 94 upstream of carbon dioxide analyzer 94 to protect the carbon dioxide analyzer 94.

Similar to carbon dioxide analyzer 80, carbon dioxide analyzer 94 may be a very sensitive analyzer and may measure carbon dioxide concentrations at parts-per-billion (ppb) levels. Carbon dioxide analyzer 94 may be particularly configured to receive the exhaust test specimen from the cooling device 88, and to determine an overall quantity of carbon dioxide of the exhaust test specimen.

From the overall quantity of carbon dioxide, the overall quantity of carbon may be determined using the following chemical balance for carbon oxidation.

$$C + O_2 = CO_2 \qquad \text{(Equation 3)}$$

With the $CO_2$ chemical balance, the mass of carbon can be calculated. Equation 4 defines carbon mass concentration measured by apparatus 10 for the simplified Equation 3.

$$C_m = \frac{3}{11} DR \times DR_{External} \times C_{CO_2} \times \rho_{CO_2} \qquad \text{(Equation 4)}$$

For equation (4), $C_m$ may be understood as the mass concentration of the carbon; DR may be understood as the total dilution ratio defined in Equation 2; $DR_{External}$ may be understood as the dilution ratio on external dilution systems, if any is used; $C_{CO_2}$ may be understood as the net molar fraction generated by the oxidation of carbon compositions; and $\rho_{CO_2}$ may be understood as the density of the $CO_2$ at standard condition. If the apparatus 10 takes the flow of engine exhaust directly from the exhaust system of a motor vehicle (i.e. raw engine exhaust), $DR_{External}$ may be understood to equal 1.0.

Using the various equations above, depending on the test situation, an overall content (mass concentration) of carbon of the exhaust sample (total carbon content) or an overall content (mass concentration) of carbon of the carbon-containing solid particles (solid carbon content) may be determined using the overall quantity of carbon of the exhaust test specimen.

As set forth above, in order to increase accuracy, carbon dioxide analyzer 80 may be used to determine a residual quantity of carbon dioxide of the exhaust test specimen. As such, after determining whether the exhaust test specimen includes a residual quantity of carbon dioxide, if the test specimen includes a residual quantity of carbon dioxide, then the residual quantity of carbon dioxide of the exhaust test specimen may be subtracted from the overall quantity of carbon dioxide of the exhaust test specimen to determine an adjusted quantity of carbon dioxide of the exhaust test specimen which may offer increased accuracy. From this, an adjusted quantity of carbon of the exhaust test specimen may be determined using the adjusted quantity of carbon dioxide of the exhaust test specimen. Furthermore, depending on the test situation, an adjusted content (mass concentration) of carbon of the exhaust sample (total carbon content) may be determined using the adjusted quantity of carbon of the exhaust test specimen, or an adjusted content (mass concentration) of carbon of the carbon-containing solid particles of the exhaust sample (solid carbon content) may be determined using the adjusted quantity of carbon of the exhaust test specimen.

The output of the foregoing carbon dioxide analyzers 80 and 94, as well as the foregoing equations and various input criteria may all be stored and utilized by a computer device 96, particularly by an electronic tangible memory and software computer programming thereof. Thus, computer device 96 may be, for example, configured to determine an overall quantity of carbon of the exhaust test specimen using the overall quantity of carbon dioxide of the exhaust test specimen received from carbon dioxide analyzer 94, which may be either a determination of total carbon content or solid carbon content.

Furthermore, the computer device 94 may be configured to determine an overall content (mass concentration) of carbon of the exhaust sample (total carbon content) or an overall content (mass concentration) of carbon of the carbon-containing solid particles (solid carbon content) using the overall quantity of carbon of the exhaust test specimen.

Moreover, after the carbon dioxide analyzer 80 or carbon dioxide analyzer 94 determines the test specimen includes a residual quantity of carbon dioxide, then the computer device 96 may be configured to subtract the residual quantity of carbon dioxide of the exhaust test specimen from the overall quantity of carbon dioxide of the exhaust test specimen to determine an adjusted quantity of carbon dioxide of the exhaust test specimen. From this, the computer device 96 may determine an adjusted quantity of carbon of the exhaust test specimen using the adjusted quantity of carbon dioxide of the exhaust test specimen. Furthermore, depending on the test situation, the computer device 96 may determine an adjusted content (mass concentration) of carbon of the exhaust sample (total carbon content) using the adjusted quantity of carbon of the exhaust test specimen, or an adjusted content (mass concentration) of carbon of the carbon-containing solid particles of the exhaust sample (solid carbon content) using the adjusted quantity of carbon of the exhaust test specimen.

As set forth above, the difference of carbon dioxide measured by carbon dioxide analyzers 94 and 80 provides an adjusted carbon dioxide determination. Under the circumstance that the carbon dioxide adsorber assembly 80 removes engine combustion generated to a negligible level, as presented in FIG. 2, carbon dioxide analyzer 80 may be eliminated with apparatus 10, and the carbon dioxide measured by carbon dioxide analyzer 94 provides the overall (unadjusted) carbon dioxide measurement.

As mentioned above, the carbon dioxide analyzer(s) 80, 94 used for apparatus 10 may have very good sensitivity. Assuming that such have a 1.0 part-per-billion (ppb) detection limit, and the apparatus 10 may be sampling from raw engine exhaust and the total dilution ratio on the apparatus 10 is 5:1, the lower detection limit on the apparatus 10 would be about 0.6 $\mu g/m^3$, translating into a raw exhaust concentration of 3 $\mu g/m^3$. This very low concentration may make the apparatus 10 capable of measuring carbon-containing solid particle emissions downstream of a diesel particulate filter (DPF) of a motor vehicle.

To enable apparatus 10 to measure carbon emissions accurately, the carbon dioxide analyzers 80, 94 may need to be calibrated periodically. Carbon dioxide span gases may be used. The calibration procedure has been well defined by industry and regulatory agencies. The calibration procedure is simple, NIST traceable, and can be automated. As a result, the apparatus may have a good accuracy for total carbon or solid carbon measurement.

The apparatus 10 may be used as a reference to calibrate other soot measurement instruments or sensors. At the outlet of the diffusion dryer 74, valve 98 is installed to provide a sample for calibrated instruments or sensors. When an instrument or sensor is calibrated with the apparatus 10, valve 98 is open. Otherwise, valve 98 is closed. By comparing measurements from calibrated soot instruments or sensors to the apparatus 10, performance of the calibrated instruments or sensors can be determined and improved.

What is claimed is:

1. A method to determine total carbon content, non-inclusive of carbon dioxide, of internal combustion engine exhaust, the method comprising:
   obtaining an engine exhaust sample from an internal combustion engine of a motor vehicle, the engine exhaust sample including carbon dioxide and one or more additional carbon-containing substances;
   diluting the exhaust sample with a diluent, wherein the diluent cools the exhaust sample and reduces a concentration of the carbon dioxide of the exhaust sample;
   removing at least 95% by weight of the carbon dioxide from at least a portion of the exhaust sample to provide an exhaust test specimen;
   heating the exhaust test specimen in a heating device to a temperature and in a presence of oxygen to oxidize at least 95% by weight the carbon of the one or more additional carbon-containing substances of the exhaust test specimen and generating carbon dioxide thereby;
   cooling the exhaust test specimen in a cooling device,
   determining an overall quantity of carbon dioxide of the exhaust test specimen; and
   determining an overall quantity of carbon of the exhaust test specimen using the overall quantity of carbon dioxide of the exhaust test specimen.

2. The method of claim 1 further comprising:
   determining an overall concentration of carbon of the exhaust sample using the overall quantity of carbon of the exhaust test specimen.

3. The method of claim 1 further comprising:
   after removing at least a substantial portion of the carbon dioxide from at least a portion of the exhaust sample to provide an exhaust test specimen, determining whether the exhaust test specimen includes a residual quantity of carbon dioxide.

4. The method of claim 3 further comprising:
   after determining whether the exhaust test specimen includes a residual quantity of carbon dioxide, if the test specimen includes a residual quantity of carbon dioxide, then subtracting the residual quantity of carbon dioxide of the exhaust test specimen from the overall quantity of carbon dioxide of the exhaust test specimen to determine an adjusted quantity of carbon dioxide of the exhaust test specimen; and
   determining an adjusted quantity of carbon of the exhaust test specimen using the adjusted quantity of carbon dioxide of the exhaust test specimen.

5. The method of claim 4 further comprising:
   determining an adjusted concentration of carbon of the exhaust sample using the adjusted quantity of carbon of the exhaust test specimen.

6. The method of claim 1 wherein:
   the one or more additional carbon-containing substances comprise at least one of carbon monoxide, one or more hydrocarbon compounds, and carbon-containing solid particles comprising one or more solid carbonaceous substances.

7. The method of claim 1 wherein:
   removing at least a substantial portion of the carbon dioxide from at least a portion of the exhaust sample to provide an exhaust test specimen is performed with at least one carbon dioxide adsorber.

8. The method of claim 7 wherein:
   the at least one carbon dioxide adsorber comprises a plurality of carbon dioxide adsorbers arranged to be operated in series.

9. A method to determine solid carbon content of internal combustion engine exhaust, the method comprising:
   obtaining an engine exhaust sample from an internal combustion engine of a motor vehicle, the engine exhaust sample including carbon dioxide, carbon-containing solid particles and one or more additional carbon-containing non-solid substances;
   heating the exhaust sample in a first heating device to a temperature and in a presence of oxygen to oxidize at least 95% by weight of the carbon of the one or more additional carbon-containing non-solid substances of the exhaust sample and generating carbon dioxide thereby;
   diluting the exhaust sample with a diluent, wherein the diluent cools the exhaust sample and reduces a concentration of the carbon dioxide of the exhaust sample;
   removing at least 95% by weight of the carbon dioxide from at least a portion of the exhaust sample to provide an exhaust test specimen;
   heating the exhaust test specimen in a second heating device to a temperature and in a presence of oxygen to oxidize at least 95% by weight of the carbon of the carbon-containing solid particles of the exhaust test specimen and generating carbon dioxide thereby;
   cooling the exhaust test specimen in a cooling device,
   determining an overall quantity of carbon dioxide of the exhaust test specimen; and
   determining an overall quantity of carbon of the exhaust test specimen using the overall quantity of carbon dioxide of the exhaust test specimen.

10. The method of claim 9 further comprising:
determining an overall concentration of carbon of the carbon-containing solid particles of the exhaust sample using the overall quantity of carbon of the exhaust test specimen.

11. The method of claim 9 further comprising:
after removing at least a substantial portion of the carbon dioxide from at least a portion of the exhaust sample to provide an exhaust test specimen, determining whether the exhaust test specimen includes a residual quantity of carbon dioxide.

12. The method of claim 11 further comprising:
after determining whether the exhaust test specimen includes a residual quantity of carbon dioxide, if the test specimen includes a residual quantity of carbon dioxide, then subtracting the residual quantity of carbon dioxide of the exhaust test specimen from the overall quantity of carbon dioxide of the exhaust test specimen to determine an adjusted quantity of carbon dioxide of the exhaust test specimen; and
determining an adjusted quantity of carbon of the exhaust test specimen using the adjusted quantity of carbon dioxide of the exhaust test specimen.

13. The method of claim 12 further comprising:
determining an adjusted concentration of carbon of the carbon-containing solid particles of the exhaust sample using the adjusted quantity of carbon of the exhaust test specimen.

14. The method of claim 9 wherein:
the one or more additional carbon-containing non-solid substances comprise at least one of carbon monoxide in gas form and one or more hydrocarbon compounds in gaseous or liquid form.

15. The method of claim 9 wherein:
the carbon-containing solid particles comprise solid soot particles.

16. The method of claim 9 wherein:
removing at least a substantial portion of the carbon dioxide from at least a portion of the exhaust sample to provide an exhaust test specimen is performed with at least one carbon dioxide adsorber.

17. The method of claim 16 wherein:
the at least one carbon dioxide adsorber comprises a plurality of carbon dioxide adsorbers arranged to be operated in series.

18. An apparatus to determine carbon content in internal combustion engine exhaust, the apparatus comprising:
an inlet configured to obtain an engine exhaust sample from an internal combustion engine of a motor vehicle;
a first heating device configured to receive the exhaust sample from the inlet, and heat the exhaust sample to a temperature and in a presence of oxygen to oxidize carbon of one or more carbon-containing non-solid substances of the exhaust sample without oxidizing carbon-containing solid particles of the exhaust sample;
a diluter configured to receive the exhaust sample from the first heating device, and to dilute the exhaust sample with a diluent which cools the exhaust sample and reduces a concentration of carbon dioxide of the exhaust sample;
at least one carbon dioxide adsorber configured to receive the exhaust sample from the diluter, and to remove carbon dioxide from at least a portion of the exhaust sample to provide an exhaust test specimen;
a second heating device configured to receive the exhaust test specimen, and heat the exhaust test specimen to a temperature and in a presence of oxygen to oxidize carbon of carbon-containing solid particles of the exhaust test specimen;
a cooling device configured to receive the exhaust test specimen from the second heating device, and cool the exhaust test specimen,
a carbon dioxide analyzer configured to receive the exhaust test specimen from the cooling device, and to determine an overall quantity of carbon dioxide of the exhaust test specimen; and
a computer device configured to determine an overall quantity of carbon of the exhaust test specimen using the overall quantity of carbon dioxide of the exhaust test specimen.

19. The apparatus of claim 18 wherein:
the computer device is further configured to determine an overall concentration of carbon of the carbon-containing solid particles of the exhaust sample using the overall quantity of carbon of the exhaust test specimen.

20. The apparatus of claim 18 wherein:
after the at least one carbon dioxide adsorber removes carbon dioxide from at least a portion of the exhaust sample to provide an exhaust test specimen, the carbon dioxide analyzer or a second carbon dioxide analyzer is configured to determine whether the exhaust test specimen includes a residual quantity of carbon dioxide.

21. The apparatus of claim 20 wherein:
after the carbon dioxide analyzer or the second carbon dioxide analyzer determines whether the exhaust test specimen includes a residual quantity of carbon dioxide, if the carbon dioxide analyzer or the second carbon dioxide analyzer determines the test specimen includes a residual quantity of carbon dioxide, then the computer device is configured to subtract the residual quantity of carbon dioxide of the exhaust test specimen from the overall quantity of carbon dioxide of the exhaust test specimen to determine an adjusted quantity of carbon dioxide of the exhaust test specimen, and the computer device configured to determine an adjusted quantity of carbon of the exhaust test specimen using the adjusted quantity of carbon dioxide of the exhaust test specimen.

22. The apparatus of claim 21 wherein:
the computer device is further configured to determine an adjusted concentration of carbon of the carbon-containing solid particles of the exhaust sample using the adjusted quantity of carbon of the exhaust test specimen.

23. The apparatus of claim 20 further comprising:
a filter configured to filter the exhaust test specimen before determining whether the exhaust test specimen includes a residual quantity of carbon dioxide.

24. The apparatus of claim 20 further comprising:
a dryer configured to remove water from the exhaust test specimen before determining whether the exhaust test specimen includes a residual quantity of carbon dioxide.

25. The apparatus of claim 18 further comprising:
a gas source comprising oxygen configured to be added to the exhaust sample prior to the exhaust sample entering the first heating device.

26. The apparatus of claim 18 wherein:
the at least one carbon dioxide adsorber comprises a plurality of carbon dioxide adsorbers arranged to be operated in series.

27. The apparatus of claim 18 further comprising:
a diluent source comprising oxygen configured to be added to the exhaust sample in the diluter.

28. The apparatus of claim 18 further comprising:
a gas source comprising oxygen configured to be added to the exhaust test specimen prior to the exhaust test specimen entering the second heating device.

29. The apparatus of claim 18 further comprising:
a filter configured to filter the exhaust test specimen after cooling the exhaust test specimen in the cooling device, and before determining the overall quantity of carbon dioxide of the exhaust test specimen.

* * * * *